(12) United States Patent
Costello et al.

(10) Patent No.: US 10,695,038 B2
(45) Date of Patent: Jun. 30, 2020

(54) DEVICES, SYSTEMS, AND METHODS FOR OBTAINING A TISSUE SAMPLE

(71) Applicant: COVIDIEN LP, Mansfield, MA (US)

(72) Inventors: David M. Costello, Delano, MN (US); Thomas D. Magnuson, Plymouth, MN (US); Michael J. Kern, St. Louis Park, MN (US)

(73) Assignee: COVIDIEN LP, Mansfield, MA (US)

( * ) Notice: Subject to any disclaimer, the term of this patent is extended or adjusted under 35 U.S.C. 154(b) by 366 days.

(21) Appl. No.: 15/018,407

(22) Filed: Feb. 8, 2016

(65) Prior Publication Data

US 2016/0302778 A1      Oct. 20, 2016

Related U.S. Application Data

(60) Provisional application No. 62/149,911, filed on Apr. 20, 2015.

(51) Int. Cl.
*A61B 10/02* (2006.01)

(52) U.S. Cl.
CPC ...... *A61B 10/0266* (2013.01); *A61B 10/0283* (2013.01)

(58) Field of Classification Search
CPC .......................... A61B 10/0266; A61B 10/0283
USPC ......................................................... 600/565
See application file for complete search history.

(56) References Cited

U.S. PATENT DOCUMENTS

| 4,051,852 A * | 10/1977 | Villari ................... A61M 39/02 604/183 |
| 4,781,202 A | 11/1988 | Janese |
| 4,785,826 A | 11/1988 | Ward |
| 4,926,877 A | 5/1990 | Bookwalter |
| 4,944,724 A * | 7/1990 | Goldberg ........... A61B 17/3401 600/486 |
| 5,074,311 A | 12/1991 | Hasson |

(Continued)

FOREIGN PATENT DOCUMENTS

| CN | 2275431 Y | 3/1998 |
| CN | 102573657 B | 10/2014 |

(Continued)

OTHER PUBLICATIONS

European Search Report, Application No. 15 16 1339 dated Jun. 15, 2015.

(Continued)

*Primary Examiner* — Daniel L Cerioni

(57) ABSTRACT

A biopsy assembly includes a catheter, a valve, a device having suction and pressure modes, and a loss of suction indicator. The catheter includes a proximal end, a distal end configured to capture a tissue sample, and defines a lumen therebetween. The valve defines a first port coupled to the device and a second port coupled to the proximal end of the catheter. When suction is applied to the first port, a suction path is defined from the distal end of the catheter through the lumen of the catheter and into the second port, such that the tissue sample is suctioned into the catheter. Upon loss of suction at the distal end, the pressure mode is used to define a pressure path from the first port to an open third port, expelling material therefrom. In the pressure mode, suction is maintained at the second port and catheter coupled thereto.

13 Claims, 3 Drawing Sheets

(56) References Cited

U.S. PATENT DOCUMENTS

| | | |
|---|---|---|
| 5,133,360 A | 7/1992 | Spears |
| 5,183,052 A | 2/1993 | Terwilliger |
| 5,267,572 A | 12/1993 | Bucalo |
| 5,649,908 A | 7/1997 | Itoh |
| 5,823,971 A | 10/1998 | Robinson et al. |
| 5,848,978 A | 12/1998 | Cecchi |
| 6,007,495 A | 12/1999 | Matula |
| 6,007,544 A | 12/1999 | Kim |
| 6,068,603 A | 5/2000 | Suzuki |
| 6,083,237 A | 7/2000 | Huitema et al. |
| 6,110,127 A | 8/2000 | Suzuki |
| 6,139,508 A | 10/2000 | Simpson et al. |
| 6,213,957 B1 | 4/2001 | Milliman et al. |
| 6,315,737 B1 | 11/2001 | Skinner |
| 6,755,793 B2 | 6/2004 | Lamoureux et al. |
| 6,792,305 B2 | 9/2004 | Rastorgoueff et al. |
| 6,875,183 B2 | 4/2005 | Cervi |
| 7,001,342 B2 | 2/2006 | Faciszewski |
| 7,033,324 B2 | 4/2006 | Giusti et al. |
| 7,137,956 B2 | 11/2006 | Nishtalas et al. |
| 7,229,439 B2 | 6/2007 | Burbank et al. |
| 7,278,970 B2 | 10/2007 | Goldenberg |
| 7,311,673 B2 | 12/2007 | Mueller, Jr. et al. |
| 8,449,478 B2 | 5/2013 | Lee et al. |
| 2009/0287114 A1 | 11/2009 | Lee et al. |
| 2010/0228221 A1* | 9/2010 | Kassab .............. A61B 17/0057 604/500 |
| 2011/0004119 A1* | 1/2011 | Hoffa ................. A61B 10/0275 600/566 |
| 2011/0208085 A1* | 8/2011 | McCullough ...... A61B 10/0275 600/565 |
| 2012/0101510 A1* | 4/2012 | Lenker ............ A61B 17/12118 606/159 |
| 2013/0331732 A1 | 12/2013 | Hoffa et al. |
| 2014/0031772 A1 | 1/2014 | Hardy et al. |
| 2014/0323910 A1 | 10/2014 | Lee |
| 2015/0272556 A1 | 10/2015 | Lee et al. |

FOREIGN PATENT DOCUMENTS

| | | |
|---|---|---|
| EP | 0 667 126 A1 | 8/1995 |
| EP | 1520518 A2 | 4/2005 |
| GB | 2338898 A1 | 1/2000 |
| WO | 8706455 A1 | 11/1987 |
| WO | 9508291 A1 | 3/1995 |
| WO | 2008115526 A2 | 9/2008 |
| WO | 2011002701 A2 | 1/2011 |

OTHER PUBLICATIONS

European Search Report EP16165259 dated Sep. 22, 2016.
CN Office Action dated Aug. 23, 2018 in corresponding CN Patent Application No. 201610244053.7, with English translation.

* cited by examiner

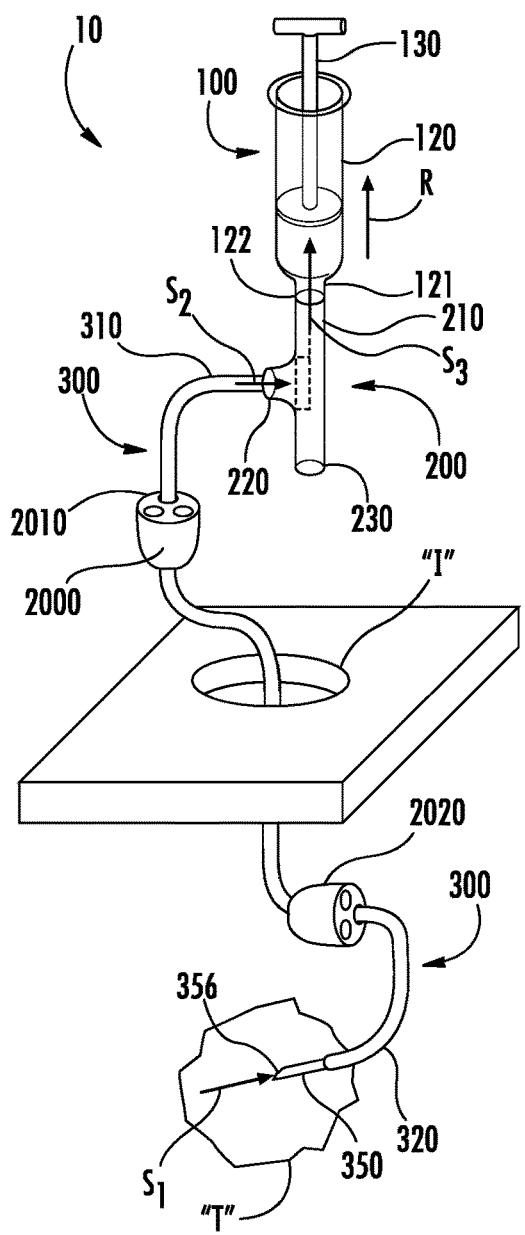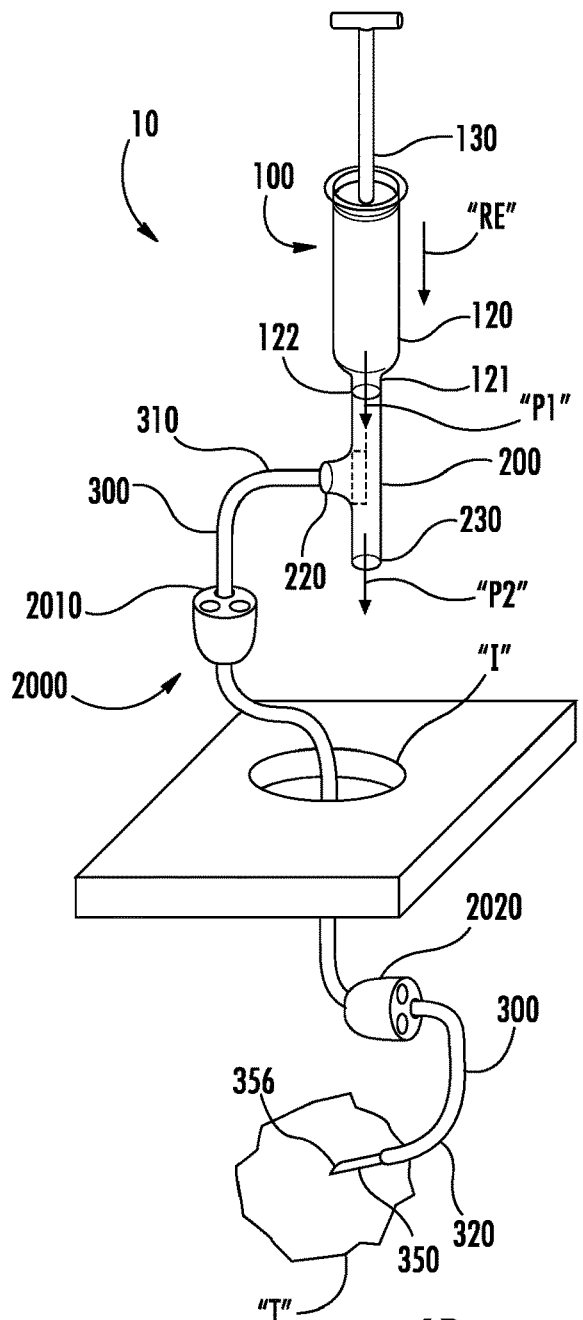
FIG. 6A
FIG. 6B

DEVICES, SYSTEMS, AND METHODS FOR OBTAINING A TISSUE SAMPLE

CROSS-REFERENCE TO RELATED APPLICATIONS

The present application claims the benefit of and priority to U.S. Provisional Application Ser. No. 62/149,911, filed Apr. 20, 2015, the entire contents of which are incorporated herein by reference.

BACKGROUND

Technical Field

The present disclosure relates generally to tissue sampling and, more particularly, to devices, systems, and methods for obtaining a tissue sample, e.g., a biopsy sample obtained via inserting a tissue-sampling device through a working channel of an endoscope.

Description of Related Art

For various medical reasons, e.g. diagnostic testing, it is often necessary for a physician, surgeon, or other medical practitioner to obtain a sample of tissue. During these sampling or biopsy procedures, the samples may be taken from a variety of organs and other soft tissue, or from a more rigid structure such as a bone or bone marrow.

There are a variety of medical procedures used to obtain a tissue sample. For example, an endoscopic procedure commonly referred to as an endoscopic biopsy procedure, is used to obtain tissue samples within a patient's body. During an endoscopic biopsy procedure, a sample of tissue is removed from a target within a patient using an endoscopic biopsy device having a tissue acquisition element. Devices or systems for visualizing the sampling procedure may also be used to facilitate obtaining the biopsy sample. For example, any radiographic, fluoroscopic, or other navigational or guidance modality, may be used for visualizing the sampling procedure.

When performing an aspiration biopsy in the lungs, for example, suction loss may occur as air from the lungs is drawn into the biopsy tool. Once suction is lost, it becomes more difficult to effectively collect tissue samples. In procedures using a syringe, if suction is lost with the syringe plunger fully retracted, the operator must depress the plunger, re-seat the device tip into tissue, and again retract the plunger. However, if the plunger is depressed while the tool is in the patient, any tissue collected prior to suction loss may be expelled back into the patient's lungs. Further, if the syringe is disconnected from the device to depress, or "recharge" the plunger, any sample collected prior to suction loss may backflow into the patient's lungs.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Provided in accordance with the present disclosure is a biopsy assembly including a biopsy catheter and a valve for retrieving a tissue sample from target tissue. The biopsy catheter includes a proximal portion, a distal portion, and defines a lumen extending therethrough. The valve defines first, second, and third ports. The first port is configured to couple to a device capable of applying suction and pressure to the valve. The second port is configured to couple to the proximal portion of the biopsy catheter. The third port is open. The valve is further configured to define a suction and pressure path. The suction path is for suctioning target tissue into the distal portion of the biopsy catheter, and the pressure path is for expelling material through the third port of the valve. When suction is applied to the first port the suction path is defined through the lumen of the biopsy catheter, the second port, and the first port. When pressure is applied to the first port the pressure path is defined through the first port and the third port. When under the pressure path suction is maintained at the second port.

The valve may further include an audible indicator configured to produce an audible output when suction is lost between the distal portion of the biopsy catheter and target tissue. According to aspects of the disclosure the audible indicator may be a whistle.

According to further aspects of the disclosure, the valve may include a visual indicator configured to produce a first visual output when suction is maintained between the distal portion of the biopsy catheter and target tissue, and a second different visual output when suction is lost between the distal portion of the biopsy catheter and target tissue. In aspects of the disclosure, the first and second visual outputs are different colors.

In accordance with further aspects of the disclosure, the distal portion of the biopsy catheter is configured to penetrate target tissue and sever a tissue sample. In yet another aspect of the disclosure, the biopsy assembly includes a coring component. The coring component includes a proximal region configured to couple to the distal portion of the biopsy catheter, and a distal region configured to penetrate target tissue and sever a tissue sample therefrom. In aspects of the disclosure, the biopsy catheter and the coring component defines a continuous lumen therethrough.

In accordance with another aspect of the disclosure, a system for obtaining a biopsy sample is provided, including a biopsy tool, a device capable of operating in a suction mode and a pressure mode, and a valve. The biopsy tool includes an elongated body having a proximal end, a distal end, and defining a lumen extending longitudinally therethrough. The valve defines a first port configured to couple to the device, a second port configured to couple to the proximal end of the biopsy tool, and an open third port. The valve is further configured to define a suction path and a pressure path. When the device operates in a suction mode the suction path is defined through the lumen of the biopsy tool, the second port of the valve, and the first port of the valve. When the device operates in a pressure mode the pressure path is defined through the first port and the third port of the valve. During the suction mode target tissue is suctioned into the distal end of the biopsy tool, and in the pressure mode material is expelled through the third port of the valve while suction is maintained at the second port of the valve.

In aspects of the disclosure, the valve further includes an audible indicator configured to produce an audible output during the suction mode when suction is lost between the distal end of the biopsy tool and the target tissue. The audible output may be a whistle.

In accordance with another aspect of the disclosure, the valve includes a visual indicator configured to produce a first and second visual output during the suction mode, the second visual output being different than the first visual output. The first visual output is produced when suction is maintained between the distal end of the biopsy tool and the target tissue. The second visual output is produced when suction is lost between the distal end of the biopsy tool and the target tissue. The first and second visual outputs may be different colors. In another aspect of the disclosure, the distal end of the biopsy tool is configured to penetrate target tissue and sever a tissue sample.

In yet another aspect of the disclosure, the system for obtaining a biopsy sample further includes a tissue sample tube connected between the biopsy tool and the valve. The tissue sample tube includes a proximal portion configured to couple to the second port of the valve, a distal portion configured to couple to the proximal end of the biopsy tool, and defines a lumen extending therebetween. The lumen is configured to capture the tissue sample therein.

According to yet another aspect of the disclosure, a method of obtaining a biopsy sample is provided. The method includes inserting a biopsy needle into a surgical site such that a distal end of the biopsy needle is in approximation to target tissue, and a proximal end of the biopsy needle is coupled to a second port of a valve. Further, a device is coupled to a first port of the valve. The method further includes applying suction to the valve using the device to create a suction path. The suction path is defined through a lumen of the biopsy needle, the second port of the valve, and the first port of the valve such that a tissue sample is suctioned into the distal end of the biopsy needle.

During the application of suction, a determination is made whether suction is lost between the distal end of the biopsy needle and target tissue. If it is determined that suction has been lost, pressure is applied to the valve using the device to create a pressure path. The pressure path is defined through the first port of the valve and a third port of the valve such that material is expelled through the third port. During the pressure path, suction is maintained at the second port. Further, suction is reapplied to the valve and suction is reestablished between the distal end of the biopsy needle and target tissue.

In accordance with an aspect of the disclosure, the device is a syringe. Applying suction with the syringe includes translating a plunger of the syringe from a proximal position towards a distal position relative to a housing of the syringe. Applying pressure with the syringe includes translating the plunger from the distal position towards the proximal position relative to the housing.

In accordance with an aspect of the disclosure, the method includes listening for an audible output to determine whether suction is lost between the distal end of the biopsy needle and the target tissue. In yet another aspect of the disclosure, the method includes looking for a visual output to determine whether suction is lost between the distal end of the biopsy needle and the target tissue.

In another aspect of the disclosure, the method further includes maintaining the distal end of the biopsy needle in approximation to target tissue while applying suction and pressure.

BRIEF DESCRIPTION OF THE DRAWINGS

Various aspects and features of the present disclosure are described hereinbelow with references to the drawings, wherein:

FIG. 6A is a prospective view of the biopsy assembly of FIG. 1 shown in use operating in a suction mode; and FIG. 6B is a prospective view of the biopsy assembly of FIG. 1 shown in use operating in a pressure mode.

DETAILED DESCRIPTION

Devices, systems, and methods for obtaining a tissue sample are provided in accordance with the present disclosure and described in detailed below. In particular, the present disclosure provides devices, systems, and methods that inhibit the loss of suction during tissue sampling procedures, obviate the need to expel any sample to regain suction should suction be lost, and provide an indication, e.g., audible and/or visual feedback, in the event of suction loss.

Figure 1:
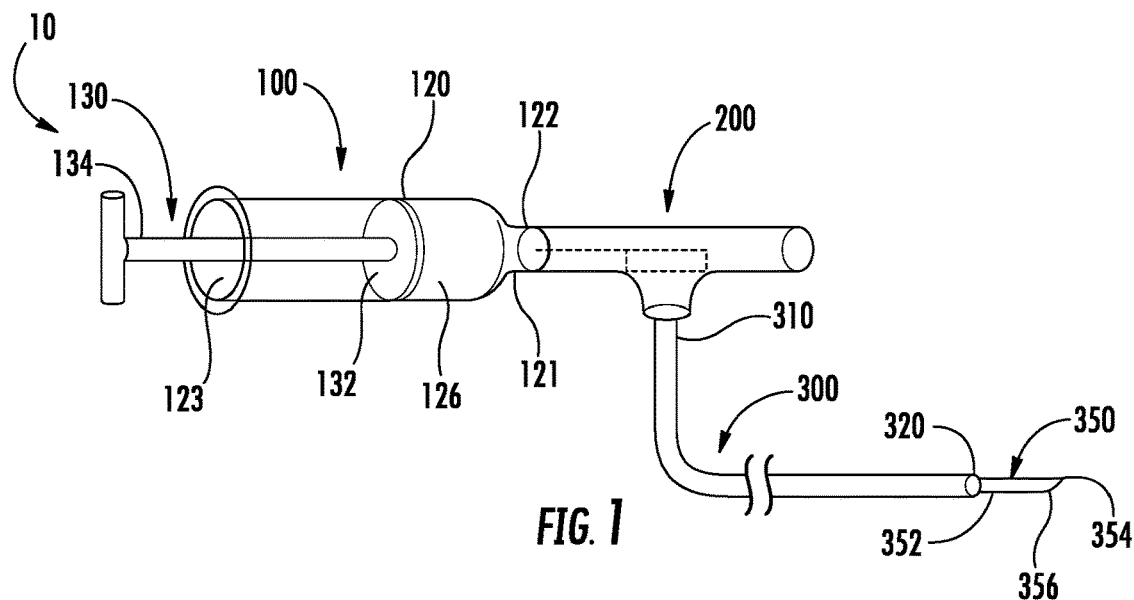
FIG. 1 is a side view of a biopsy assembly provided in accordance with the present disclosure.

With initial reference to FIG. 1, a biopsy assembly 10 provided in accordance with the present disclosure is shown generally including a suction device 100, a valve 200, and a biopsy catheter 300. Although the present disclosure will be described herein with reference to specific types of biopsy devices and procedures, namely endoscopic biopsy devices and procedures, it should be appreciated that the aspects and features of the present disclosure may be used in conjunction with any suitable biopsy or tissue sampling devices and procedures.

Continuing with reference to FIG. 1, it is envisioned that suction device 100 may take the form of any suitable device capable of creating a suction and pressure path, for example, a pump or syringe. For purposes herein, suction device 100 will be described as a syringe 100. Syringe 100 includes a tubular housing 120 and a plunger 130 configured to be slidably received within tubular housing 120. Tubular housing 120 defines a connecting port 122 disposed at a first end 121, an open second end 123, and an elongated cavity 126 therebetween. Connecting port 122 may be configured as a threaded shaft or threaded lumen, a male or female luer lock adaptor, or any other suitable structure configured to releasably mate with a counterpart device, such as valve 200, as described below.

Plunger 130 includes a circular portion 132 configured to be inserted into tubular housing 120 and a handle 134 extending proximally therefrom. With plunger 130 inserted into tubular housing 120, a fluid tight seal is created between a circumference of circular member 132 and an inner surface of tubular housing 120. It is envisioned that tubular housing 120 and circular portion 132 be made from any suitable material and/or include suitable components to facilitate the creation of the fluid tight seal therebetween, e.g., by forming circular portion 132 at least partially from a resiliently flexible material or providing an O-ring about the circumference of circular portion 132. As plunger 130 slides within tubular housing 120 between first and second ends 121, 123 thereof, suction or pressure is created at connecting port 122, depending upon the direction of travel of plunger 130 relative to tubular housing 120.

Tubular housing 120 may include one or more ergonomic features to facilitate gripping and manipulation of plunger 130, such as ridge 128 which extends radially from open second end 123. Plunger 130 may further include a locking device (not shown) enabling the position of plunger 130 with respect to first end 121 of tubular housing 120 to be fixed in one or more incremental positions, thereby maintaining a steady suction or pressure at connecting port 122 of tubular housing 120.

Figure 2:
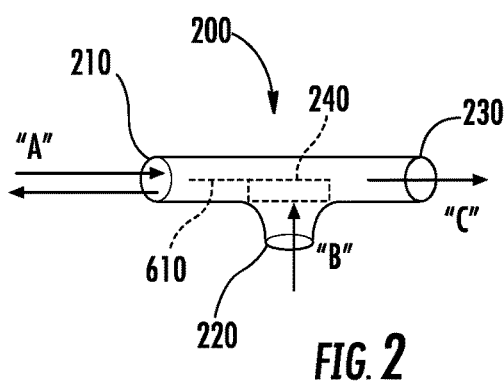
FIG. 2 is a side view of a valve of the biopsy assembly of FIG. 1.

With reference to FIG. 2, valve 200 is configured as a three-way directional-control valve defining a first port 210, a second port 220, a third port 230, and a flow controller 240. Valve 200 may define a "T" configuration, as illustrated in FIG. 2, or may define any other suitable configuration such that first, second, and third ports 210, 220, and 230 are accessible, e.g., a "Y" configuration. Valve 200 is configured to permit the flow of material through first, second, and third ports 210, 220, and 230 as described below. First, second, and third ports 210, 220, and 230 are configured to mate with syringe 100, biopsy catheters 300, and a surgical tool, respectively. A variety of surgical tools, for example, biopsy needles, specimen collection tubes, hypodermic needles, connecting tubing, etc. may be configured to mate with third port 230. First, second, and third ports 210, 220, and 230 may include threaded shafts or threaded lumens, male or female luer lock adaptors, or any other suitable structure configured to facilitate mating of the respective port 210, 220, and 230 with a corresponding device or component thereof.

Flow controller 240 is disposed within valve 200 and serves to selectively direct the flow of material through second port 220 and third port 230. Specifically, while flow controller 240 permits the flow of material through first port 210 in both directions, as indicated by arrows "A," flow controller 240 serves to permit material to flow through second port 220 only in the direction of arrow "B" into valve 200 and serves to permit material to flow through third port 230 only in the direction of arrow "C" out of valve 200. Further, flow controller 240 is configured such that as material is expelled from third port 230, second port 220 is sealed off to inhibit expulsion of material from second port 220 and maintain suction at second port 220. Such a feature is important in that it allows for the re-charging of syringe 100 without having to expel any portion of a tissue sample and without losing suction on the tissue sample, as described more fully below. Flow controller 240 may be configured as a duckbill valve, a check valve, a spool valve, or any other valve capable of providing the above-detailed features.

Referring again to FIG. 1, biopsy catheter 300 includes a proximal end 310, a distal end 320, and defines a lumen extending therethrough. Proximal end 310 is configured to couple to second port 210 of valve 200 in any suitable fashion, e.g., threaded connection, luer lock, press-fit, etc. Distal end 320 of biopsy catheter 300 is configured to receive a tissue sample from target tissue "T" (FIGS. 6A and 6B). It should be appreciated that with biopsy catheter 300 coupled to valve 200, a fluid-tight channel is established between distal end 320 of biopsy catheter 300 and second port 220 of valve 200 to enable a tissue sample to be suctioned into biopsy catheter 300 by actuating suction device 100, e.g., moving plunger 130 relative to tubular housing 120.

The distal end 320 of biopsy catheter 300 may further be coupled to, or integrally formed with, a tissue coring element 350. Tissue coring element 350 is configured to engage target tissue "T" (FIGS. 6A and 6B) and facilitate the removal of a sample of the target tissue "T" (FIGS. 6A and 6B). The coring component 350 may define a longitudinal lumen extending from a proximal region 352 and terminating in a distal opening 354. It should be appreciated that with biopsy catheter 300 and tissue coring element 350 coupled, the respective lumens act cooperatively to define a single fluid-tight channel between the distal opening 354 of the tissue coring element 350 and the proximal end 310 of the biopsy catheter 300. The coring element 350 may be configured similar to any of the coring elements disclosed in U.S. patent application Ser. No. 14/564,779, filed on Dec. 9, 2014, the entire contents of which are incorporated herein by reference.

Figure 3:
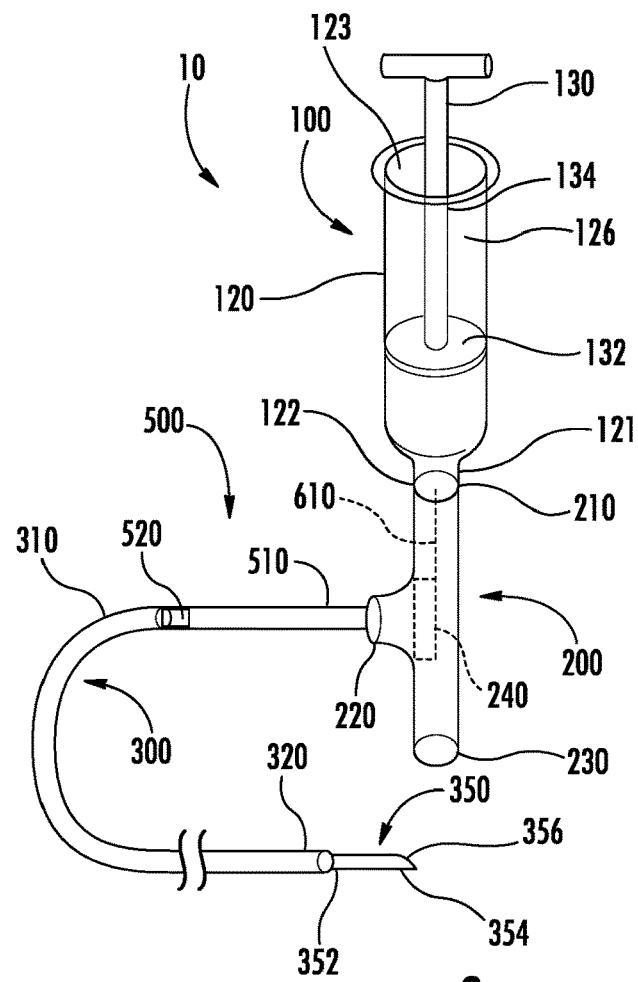
FIG. 3 is a side view of the biopsy assembly of FIG. 1 further including a sample tube coupled thereto.

With reference to FIG. 3, in some embodiments a sample collection tube 500 configured for use with biopsy assembly 10 is provided to collect and retain tissue samples captured by biopsy assembly 10. Sample collection tube 500 includes a proximal end 510, a distal end 520, and defines a lumen therethrough. Sample collection tube 500 may be positioned between biopsy catheter 300 and valve 200 such that the proximal end 310 of biopsy catheter 300 is coupled to the distal end 520 of sample collection tube 500, and the proximal end 530 of sample collection tube 500 is coupled to second port 220 of valve 200. It should be appreciated that with sample collection tube 500 coupled between biopsy catheter 300 and valve 200, a fluid-tight channel is established between the distal end 320 of the biopsy catheter 300 and the second port 220 of the valve 200. Alternatively, sample collection tube 500 may be coupled to third port 230 of valve 200. Sample collection tube 500 may be coupled to biopsy catheter 300 and valve 200 in any suitable fashion, such as those detailed above.

Figure 4:
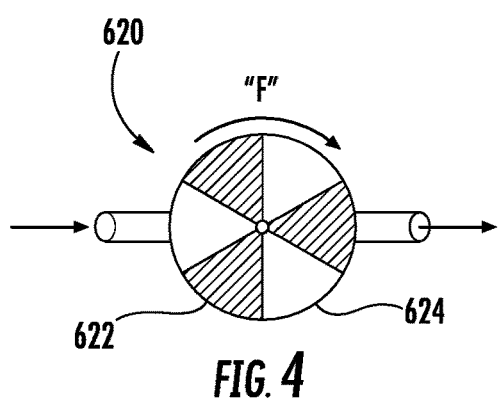
FIG. 4 is a side view of a visual indicator of the biopsy assembly of FIG. 1.

Referring to FIGS. 1, 2, and 4, biopsy assembly 10 further includes one or more indicators 610, 620 used to notify a user of a loss of suction with the target tissue "T" (FIGS. 6A and 6B) at the distal end 320 of biopsy catheter 300. A loss of suction may occur if, for example, the distal end 320 of biopsy catheter 300 is not maintained in approximation to the target tissue "T" (FIGS. 6A and 6B). The one or more indicators 610, 620 may be positioned in line with the flow of material, from the distal end 320 of biopsy catheter 300 through valve 200 and into syringe 100. Alternatively, the one or more indicators 610, 620 may be disposed at least partially within valve 200, for example, between first port 210 and second port 220.

In embodiments, the indicator is an audible indicator 610, as shown in FIG. 2, that is configured to emit a whistle, siren, click, or any other suitable auditory notification upon a free flow of material therethrough, indicating a loss of suction, e.g., due to loss of approximation between the distal end 320 of biopsy catheter 300 and the target tissue "T" (FIGS. 6A and 6B). As seen in FIG. 4, the indicator may additionally or alternatively include a visual indicator 620, such that, upon a free flow of material therethrough, a first visual pattern will change to a second, different visual pattern indicating to the user that suction has been lost. In embodiments, the first and second visual patterns are represented by different colors, written warnings, or any other suitable visual indicia. Visual indicator 620, as shown in FIG. 4, is configured as an in-line flow indicator where the colored segment 622 of the rotatable wheel 624 turns in the direction of arrow "F" as material passes therethrough, visually indicating to the user that suction has been lost.

It is envisioned that a navigation tool, such as a navigation catheter, an endoscope, or any other articulatable surgical device, may be included to facilitate the positioning of the distal end 320 of biopsy catheter 300. The navigation tool may be used as an avenue for guiding working tools, including biopsy catheter 300, into close approximation with target tissue "T" (FIGS. 6A and 6B). In exemplary embodiments a navigation catheter 2000 is provided and biopsy catheter 300 may be introduced into a lumen 2010 of navigation catheter 2000. A locatable guide (LG) (not shown) may additionally be inserted into the navigation tool to facilitate approximation to the target tissue "T" (FIGS. 6A and 6B). Alternatively, navigation catheter 2000, biopsy catheter 300, or tissue coring element 350 may have a sensor (not shown) embedded therein to enable tracking and navigation to the target "T" (FIGS. 6A and 6B). Further, a fiber optic or other scope may be included to provide visual cues to the operator during a biopsy procedure.

Figure 5:
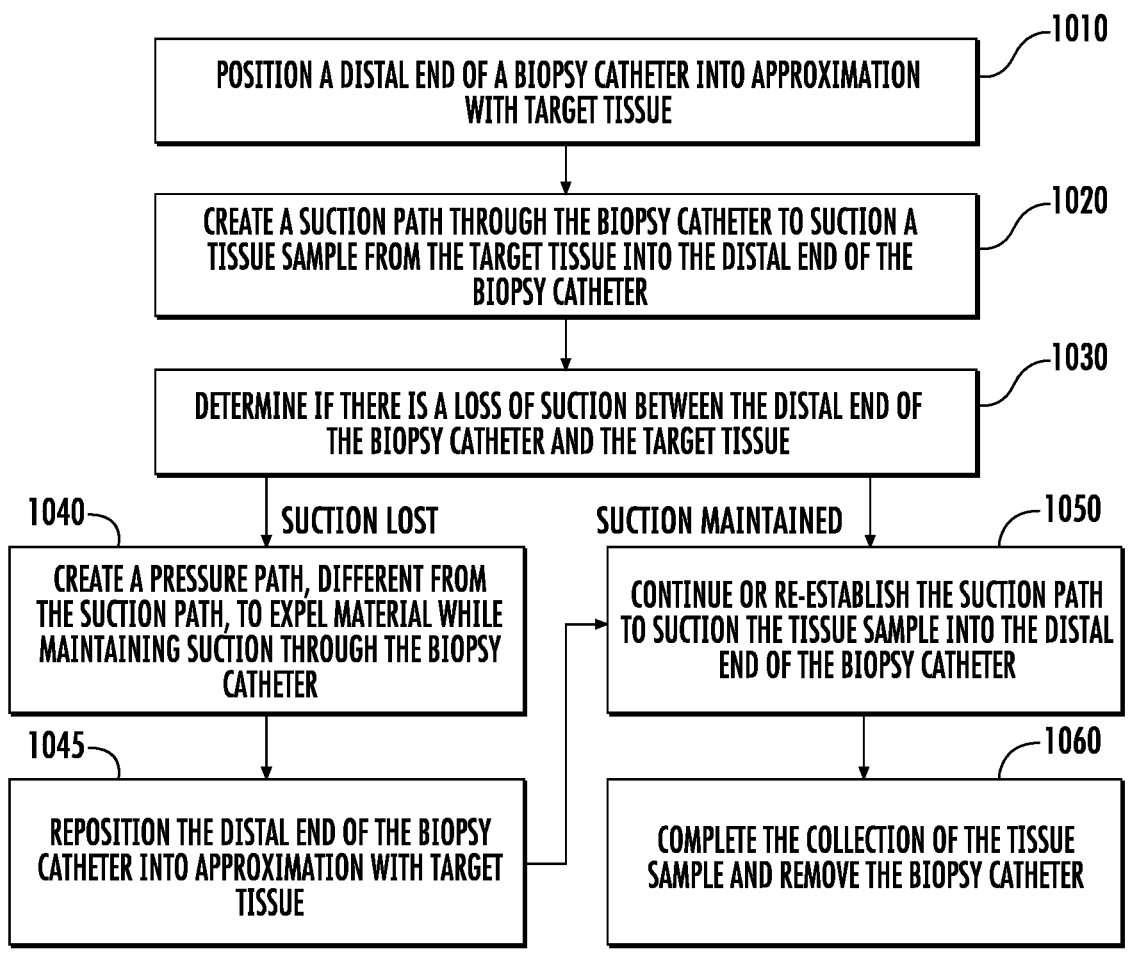
FIG. 5 is a flowchart illustrating a sampling procedure provided in accordance with the present disclosure.

With reference to FIGS. 5-6B, the operation of biopsy assembly 10 is described. Initially, in step 1010, the distal end 320 of biopsy catheter 300 is inserted into the target tissue "T" to be sampled. Prior to or after inserting biopsy catheter 300 into position, the proximal end 310 of biopsy catheter 300 is coupled to the second port 220 of valve 200 and valve 200 is coupled to syringe 100.

In step 1020, the syringe 100 (or other suitable suction apparatus) is operated in a suction move via slidably retracting plunger 130 from the first end 121 of tubular housing 120 to create a suction path defined from the distal end 320 of biopsy catheter 300, through the lumen of biopsy catheter 300, through second port 220, and through first port 210 such that a tissue sample from the target tissue "T" is suctioned into the distal end 320 of the biopsy catheter 300. The suction path is indicated by arrows "$S_1$," "$S_2$," and "$S_2$" as the plunger 130 is retracted in the direction of arrow "R" (FIG. 6A). It is envisioned that plunger 130 may be locked in one or more positions during retraction using the locking device (not shown) to fix the position of plunger 130 with respect to the first end 121 of tubular housing 120 and maintain suction at the distal end 320 of biopsy catheter 300.

During the suctioning of the tissue sample into biopsy catheter 300, it is determined whether a loss of suction with the target tissue "T" has occurred, as indicated in step 1030. More specifically, by listening for an audible output from indicator 610 and/or viewing indicator 620 for a visual output, the user can be alerted to the loss of suction, as detailed above.

Should suction be lost, as indicated in step 1040, syringe 100 is put into a pressure mode to create a pressure path defined from first port 210 of valve 200 to third port 230 of valve 230, thereby expelling any material, e.g., air, drawn into syringe 100 as a result of the loss of suction. The pressure mode of syringe 100 is accomplished by slidably moving plunger 130 towards the first end 121 of tubular housing 120, known as "recharging" plunger 130 of syringe 100. The pressure path is indicated by arrows "$P_1$" and "$P_2$" as plunger 130 is recharged in the direction of arrow "RE" of FIG. 6B. Once recharging is complete and the air expelled from syringe 100, the distal end 320 of biopsy catheter 300 can be repositioned within the target tissue "T" to regain suction, as indicated in step 1045. As detailed above, during the recharging of plunger 130, valve 200 maintains suction at second port 220, thereby maintaining suction through the lumen of biopsy catheter 300 and inhibiting loss of tissue sample already collected.

In step 1050, once suction is reestablished (or in instances where suction has not been lost), syringe 100 may be further operated in a similar fashion as described above to suction a sufficient amount of tissue sample into biopsy catheter 300. Once a sufficient tissue sample has been acquired, biopsy catheter 300 may be removed from the patient, as indicated in step 1060.

Furthermore, while various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. All patents and publications discussed herein are incorporated in their entirety by reference thereto.

What is claimed is:

1. A biopsy assembly comprising:
   a biopsy catheter including a proximal portion, a distal portion, and defining a lumen extending therethrough;
   a valve defining a first port, a second port, and a third port in-line with the first port and forming an open distal end, the first port configured to couple to a device that applies suction and pressure to the valve, and the second port configured to couple to the proximal portion of the biopsy catheter; and
   a flow controller disposed within the valve and configured to direct a flow of target tissue through the second and third ports,
   wherein the valve includes a suction indicator configured to indicate whether or not the suction is lost between the distal portion of the biopsy catheter and the target tissue,
   wherein the valve is configured such that, when suction is applied to the first port, a suction path is defined through the lumen of the biopsy catheter, the second port, and the first port for suctioning the target tissue into an intersection of the first, second, and third ports from the distal portion of the biopsy catheter, and
   wherein when the suction indicator indicates that the suction is lost, pressure is applied to the first port to form a pressure path through the first port and the third port and the flow controller directs the flow of the target tissue along the pressure path from the intersection to the open distal end of the third port to expel the target tissue while maintaining suction at the second port.

2. The biopsy assembly of claim 1, wherein the suction indicator is an audible indicator configured to produce an audible output when the suction is lost between the distal portion of the biopsy catheter and target tissue.

3. The biopsy assembly of claim 2, wherein the audible indicator is a whistle.

4. The biopsy assembly of claim 1, wherein the valve further includes a visual indicator configured to produce a first visual output when suction is maintained between the distal portion of the biopsy catheter and target tissue and a second, different visual output when suction is lost between the distal portion of the biopsy catheter and target tissue.

5. The biopsy assembly of claim 4, wherein the first and second visual outputs are different colors.

6. The biopsy assembly of claim 1, wherein the distal portion of the biopsy catheter is configured to penetrate target tissue and sever a tissue sample therefrom.

7. The biopsy assembly of claim 1, further including a coring component including a proximal region configured to couple to the distal portion of the biopsy catheter, and a distal region configured to penetrate target tissue and sever a tissue sample therefrom.

8. The biopsy assembly of claim 7, wherein each of the biopsy catheter and the coring component defines a continuous lumen therethrough.

9. The biopsy assembly according to claim 1, wherein the flow controller is configured to seal off the second port when pressure is applied to the first port.

10. The biopsy assembly according to claim 1, wherein the flow controller is one of a duckbill valve, a check valve, or a spool valve.

11. A biopsy assembly comprising:
- a biopsy catheter defining a lumen;
- a valve defining a first port, a second port fluidly coupled to the lumen, and a third port in-line with the first port and having an open end, the first port configured to couple to a suction device for suctioning tissue into an intersection of the first, second, and third ports and for generating a pressure path through the first and third ports; and
- a flow controller disposed within the valve and configured to direct the flow of tissue along the pressure path from the intersection to the open end of the third port while maintaining a suction at the second port,
- wherein the valve includes a suction indicator configured to indicate whether or not the suction is lost between a distal portion of the biopsy catheter and the tissue, and
- wherein when the suction indicator indicates that the suction is lost, the flow controller directs the flow of tissue along the pressure path to the open end of the third port while maintaining the suction at the second port.

12. The biopsy assembly according to claim 11, wherein the flow controller is configured to seal off the second port while directing the flow of tissue along the pressure path from the intersection to the open end of the third port.

13. The biopsy assembly according to claim 11, wherein the flow controller is configured to permit the flow of tissue through the second port into the valve and to prevent the flow of tissue through the second port into the lumen.

* * * * *